US00PP34330P2

(12) United States Plant Patent
Schoemaker

(10) Patent No.: US PP34,330 P2
(45) Date of Patent: Jun. 14, 2022

(54) ***HYDRANGEA* PLANT NAMED 'LC NO15'**

(50) Latin Name: *Hydrangea paniculata*
Varietal Denomination: LC NO15

(71) Applicant: Alex Frederick Schoemaker, Boskoop (NL)

(72) Inventor: Alex Frederick Schoemaker, Boskoop (NL)

(73) Assignee: ALEX SCHOEMAKER LIVING CREATIONS HOLDING B.V., Boskoop (NL)

( * ) Notice: Subject to any disclaimer, the term of this patent is extended or adjusted under 35 U.S.C. 154(b) by 0 days.

(21) Appl. No.: 17/512,408

(22) Filed: Oct. 27, 2021

Related U.S. Application Data

(60) Provisional application No. 63/116,829, filed on Nov. 21, 2020.

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

PUBLICATIONS

CPVO Register. https://online.plantvarieties.eu/public-ConsultationDetails?registerId=20200385&denomination=LC%20NO15. 2 pages (Year: 2021).*

* cited by examiner

*Primary Examiner* — Karen M Redden
(74) *Attorney, Agent, or Firm* — C. Anne Whealy

(57) ABSTRACT

A new and distinct cultivar of *Hydrangea* plant named 'LC NO15', characterized by its relatively compact, upright to outwardly spreading and uniform plant habit; freely branching habit with strong lateral branches; freely flowering habit with plants remaining in flower for a long period of time; large and strong inflorescences with large white-colored sterile flowers that become purplish red with subsequent development; and good garden performance.

2 Drawing Sheets

Figure 1:
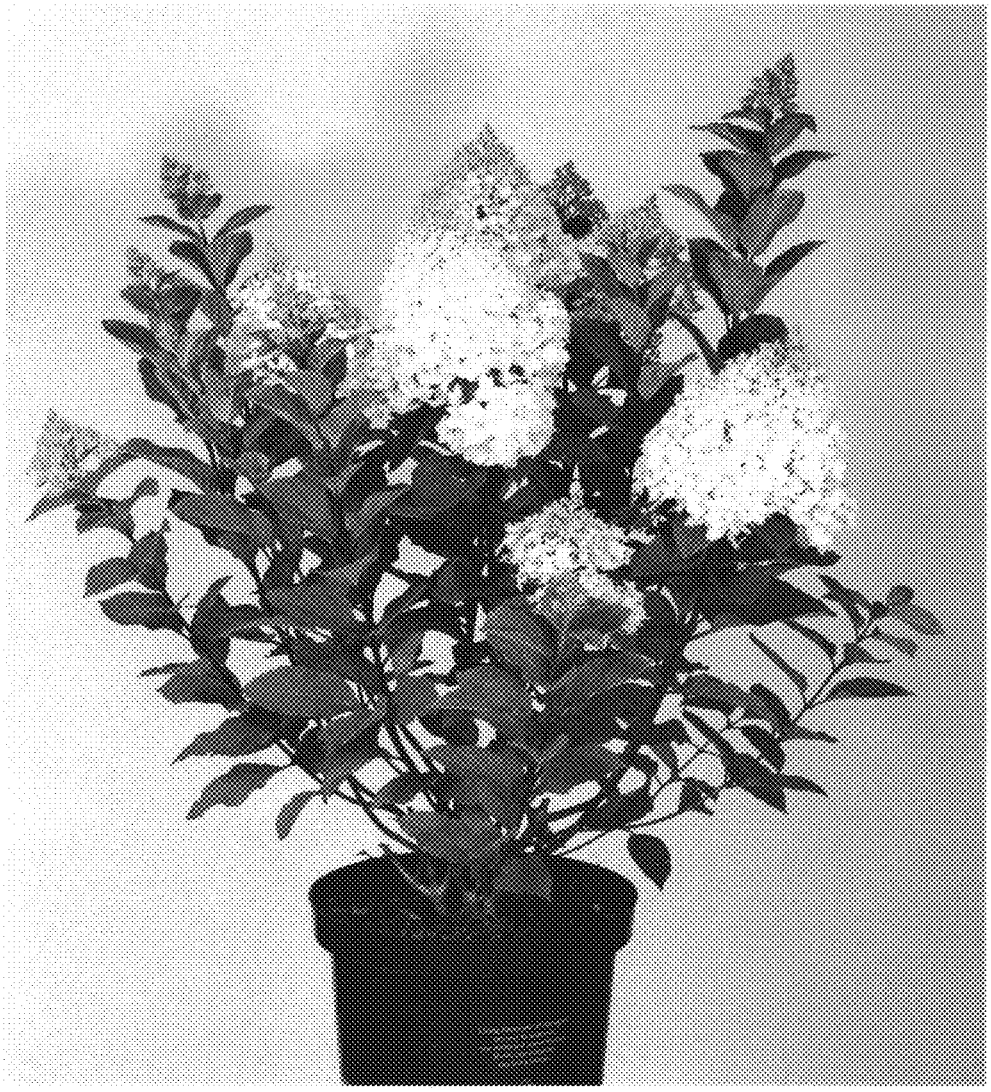

Botanical designation: *Hydrangea paniculata.*
Cultivar denomination: 'LC NO15'.

CROSS-REFERENCED TO CLOSELY RELATED APPLICATIONS

Title: *Hydrangea* Plant Named 'LC NO15'
Inventor/Applicant: Alex Frederick Schoemaker
Provisional application Ser. No.: 63/116,829
Filed: Nov. 21, 2020
Inventor/Applicant hereby claims the benefit of this Provisional U.S. Patent Application.

STATEMENT REGARDING PRIOR DISCLOSURES BY INVENTOR/APPLICANT

An European Community Plant Breeder's Rights application for the instant plant was filed by the Inventor/Assignee, Mr. Alex Frederick Schoemaker of Boskoop, The Netherlands on Feb. 6, 2020, application number 2020/0385. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO15'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from a cross-pollination made by the Inventor in July, 2016 in Boskoop, The Netherlands, of *Hydrangea paniculata* 'Magical Candle', not patented, as the female, or seed, parent with *Hydrangea paniculata* 'DVP Pinky', disclosed in U.S. Plant Pat. No. 16,166, as the male, or pollen, parent. The new *Hydrangea* plant was discovered and selected by the Inventor as a single flowering plant from within the progeny of the stated cross-pollination in a controlled greenhouse environment in Boskoop, The Netherlands in July, 2018.

Asexual reproduction of the new *Hydrangea* plant by softwood terminal cuttings in a controlled greenhouse environment in Boskoop, The Netherlands since August, 2018 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO15'. These characteristics in combination distinguish 'LC NO15' as a new and distinct *Hydrangea* plant:

1. Relatively compact, upright to outwardly spreading and uniform plant habit.
2. Freely branching habit with strong lateral branches.
3. Freely flowering habit with plants remaining in flower for a long period of time.
4. Large and strong inflorescences with large white-colored sterile flowers that become purplish red with subsequent development.
5. Good garden performance.

Plants of the new *Hydrangea* can be compared to plants of the female parent, 'Magical Candle'. Plants of the new *Hydrangea* differ primarily from plants of 'Magical Candle' in plant habit as plants of the new *Hydrangea* are broader than and not as upright as plants of 'Magical Candle'. In addition, leaf apices of plants of the new *Hydrangea* are more acute than leaf apices of plants of 'Magical Candle'.

Plants of the new *Hydrangea* can be compared to plants of the male parent, 'DVP Pinky'. Plants of the new *Hydrangea* differ primarily from plants of 'DVP Pinky' in flowering habit as inflorescences of plants of the new *Hydrangea* are denser and have more flowers than inflorescences of plants of 'DVP Pinky'.

Plants of the new *Hydrangea* can also be compared to plants of the *Hydrangea paniculata* 'LC NO12', disclosed in U.S. Plant Pat. No. 33,256. In side-by-side comparisons, plants of the new *Hydrangea* differ primarily from plants of 'LC NO12' in plant and growth habit as plants of the new *Hydrangea* are more compact and shorter than plants of 'LC NO12'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'LC NO15' grown in a container.

Figure 2:
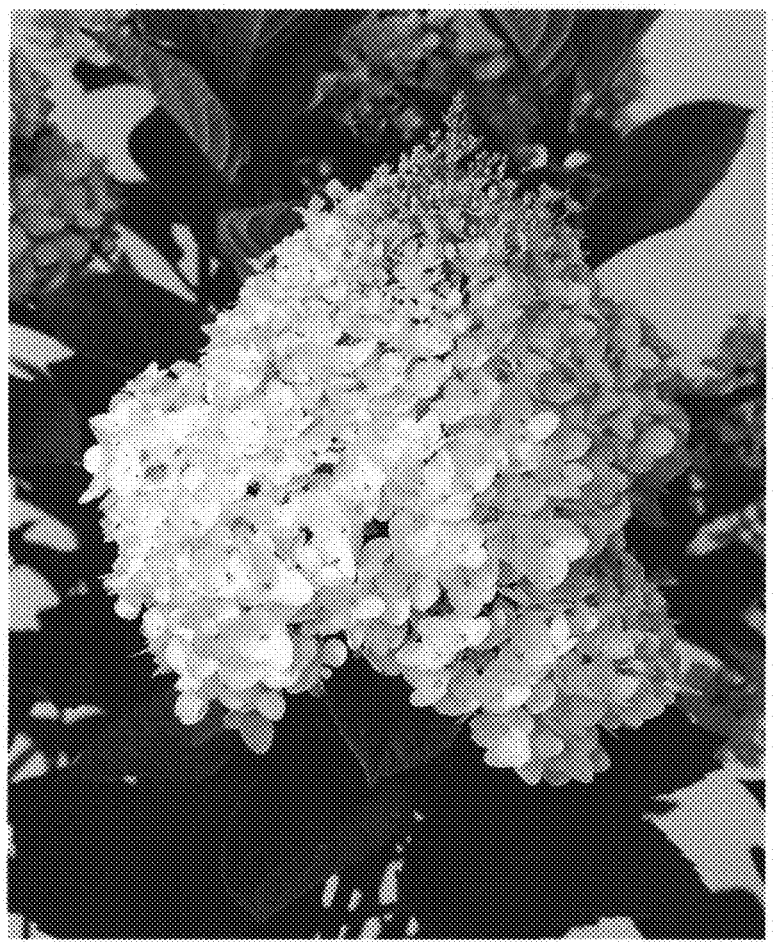
Figure 3:
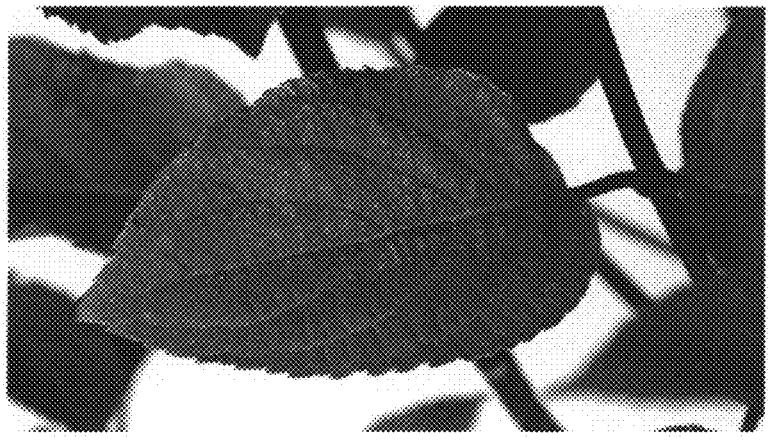

The photograph at the top of the second sheet (FIG. 2) is a close-up view of a typical inflorescence of 'LC NO15' and the photograph at the bottom of the second sheet (FIG. 3) is a close-up view of a typical leaf of 'LC NO15'.

DETAILED BOTANICAL DESCRIPTION

Plants used in the aforementioned photographs and in the following description were grown during the late summer in 28-cm containers in an outdoor nursery in Boskoop, The Netherlands and under cultural practices typical of commercial *Hydrangea* production. During the production of the plants, day temperatures ranged from about 16° C. to 26° C. and night temperatures ranged from about 8° C. to 20° C. Plants of the new *Hydrangea* were pruned one time and were three years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO15'.

Parentage:

*Female, or seed, parent.*—*Hydrangea paniculata* 'Magical Candle', not patented.

*Male, or pollen, parent.*—*Hydrangea paniculata* 'DVP Pinky', disclosed in U.S. Plant Pat. No. 16,166.

Propagation:

*Type cutting.*—By softwood terminal cuttings.

*Time to initiate roots, summer.*—About 16 days at temperatures about 16° C. to 30° C.

*Time to produce a rooted young plant, summer.*—About 120 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact, upright to outwardly spreading and uniform plant habit; overall plant shape, broadly obovate; strong and sturdy stems; moderately vigorous growth habit and moderate to high growth rate.

*Plant height.*—About 75.4 cm.

*Plant diameter or area of spread.*—About 77.5 cm.

Lateral branch description:

*Branching habit.*—Freely branching, after pruning, about 20 lateral branches develop per plant.

*Length.*—About 46.8 cm.

*Diameter.*—About 6 mm.

*Internode length.*—About 4.8 cm.

*Texture.*—When developing, moderately pubescent; fully developed, woody.

*Aspect.*—Upright to about 60° from vertical.

*Strength.*—Strong, sturdy.

*Color, when developing.*—Close to 187C.

*Color, developed.*—Close to N199B and 200D; when woody, close to 197A, 199A and N199A.

*Lenticels.*—Density: Moderate on developing stems; not visible on developed stems. Size: About 1.25 mm by 0.75 mm. Color: Close to 164B and 164C.

Leaf description:

*Arrangement.*—Opposite or in whorls of three, simple.

*Length.*—About 10.3 cm.

*Width.*—About 6.7 cm.

*Shape.*—Ovate.

*Apex.*—Apiculate to acute.

*Base.*—Short attenuate to obtuse.

*Margin.*—Serrate; slightly undulate.

*Texture, upper surface.*—Sparsely pubescent.

*Texture, lower surface*.—Moderately pubescent.

*Venation pattern*.—Pinnate.

*Color*.—Developing leaves, upper surface: Close to 143A to 143B. Developing leaves, lower surface: Close to a blend of 145A and 146D. Fully developed leaves, upper surface: Close to a blend of 143A and 146B; venation, close to N148B. Fully developed leaves, lower surface: Close to a blend of 145A and 146D; venation, close to 195B to 195C.

*Petioles*.—Length: About 1.9 cm. Diameter: About 3 mm. Texture and luster, upper surface: Moderately pubescent; slightly glossy. Texture and luster, lower surface: Sparsely pubescent; slightly glossy. Color, upper surface: Close to 183A. Color, lower surface: Close to 177D and 183A.

Flower description:

*Flower type and habit*.—Showy rotate sterile flowers and smaller inconspicuous rotate fertile flowers arranged on terminal panicles; panicles dense and broadly conical in shape; sterile flowers face upright to outwardly and slightly drooping depending on their position in the inflorescence; fertile flowers face mostly upright.

*Fragrance*.—Moderately fragrant; sweet and pleasant.

*Natural flowering season*.—Flowering begins in the midsummer and is continuous until late summer in Northern Europe.

*Flower longevity*.—Sterile flowers last about six weeks on the plant, sterile flowers persistent; fertile flowers last about five days on the plant, fertile flowers not persistent.

*Quantity of flowers*.—Freely flowering habit; about 1,000 sterile flowers and about 335 fertile flowers per panicle.

*Panicle height*.—About 20.7 cm.

*Panicle diameter*.—About 18.6 cm.

*Inflorescence peduncles*.—Length: About 18.2 cm. Diameter: About 3.5 mm. Strength: Moderate. Aspect: Upright to about 47.5° from vertical. Texture and luster: Moderately pubescent; matte. Color: Close to 185C.

*Sterile flower buds*.—Length: About 4 mm. Diameter: About 1.2 cm. Shape: Broadly cup-shaped. Color: Close to 157A to 157B; immature petals, close to 59C.

*Fertile flower buds*.—Length: About 4 mm. Diameter: About 3 mm. Shape: Broadly obovate. Color: Close to NN155B, distally tinged with close to 62B; immature calyx, close to 157C; immature ovary, close to 157A.

*Sterile flower diameter*.—About 2.4 cm.

*Sterile flower depth* (*height*).—About 5 mm.

*Fertile flower diameter*.—About 9.5 mm.

*Fertile flower depth* (*height*).—About 6 mm.

*Petals, sterile flowers:*.—Quantity and arrangement: Typically four arranged in a single whorl. Length: About 3.5 mm. Width: About 1.5 mm. Shape: Ovate. Apex: Acute. Base: Cuneate. Margin: Entire. Texture and luster, upper and lower surfaces: Smooth, glabrous; matte. Color: When opening, upper surface: Close to NN155D. When opening, lower surface: Close to NN155D; distally, close to 62B. Fully opened, upper and lower surfaces: Close to NN155D; color does not change with subsequent development.

*Petals, fertile flowers*.—Quantity and arrangement: Typically five arranged in a single whorl. Length: About 4 mm. Width: About 1.75 mm. Shape: Ovate; moderately concave. Apex: Acute. Base: Cuneate. Margin: Entire. Texture and luster, upper and lower surfaces: Smooth, glabrous; slightly glossy. Color: When opening and fully opened, upper surface: Close to 155C and NN155B; color does not change with subsequent development. When opening and fully opened, lower surface: Close to 155C and NN155B; distally, slightly tinged with close to 62D; color does not change with subsequent development.

*Sepals, sterile flowers*.—Quantity and arrangement: Typically four or occasionally five arranged in a single whorl. Length: About 1.5 cm. Width: About 1.25 cm. Shape: Broadly ovate. Apex: Obtuse. Base: Cuneate. Margin: Entire. Texture and luster, upper and lower surfaces: Smooth, glabrous; matte. Color: When opening, upper and lower surfaces: Close to 155C. Fully opened, upper surface: Close to 155A; with subsequent development, color becoming closer to 58B. Fully opened, lower surface: Close to 155C; with subsequent development, color becoming closer to 63B and towards the base, close to 157A.

*Sepals, fertile flowers*.—Quantity and arrangement: Typically five in a single whorl. Length: About 1 mm. Width: About 1.2 mm. Shape: Broadly deltoid. Apex: Broadly acuminate. Base: Broadly cuneate. Margin: Entire. Texture and luster, upper and lower surfaces: Smooth, glabrous; matte. Color: When opening, upper and lower surfaces: Close to 157C. Fully opened, upper and lower surfaces: Close to 157D; color does not change with subsequent development.

*Pedicels, sterile flowers*.—Length: About 1.9 cm. Diameter: About 1 mm. Strength: Moderately strong. Aspect: About 45° from branch axis. Texture and luster: Moderately pubescent; matte. Color: Close to 157C.

*Pedicels, fertile flowers*.—Length: About 2 mm. Diameter: About 0.5 mm. Strength: Moderately strong. Aspect: About 5° from vertical. Texture and luster: Moderately pubescent; matte. Color: Close to 157D.

*Reproductive organs, sterile flowers*.—Stamens: Quantity per flower: About eight. Filament length: About 3.5 mm. Filament color: Close to NN155B. Anther length: About 0.75 mm. Anther shape: Broadly oblong. Anther color: Close to 158D to lighter than 158D. Pollen amount: Moderate. Pollen color: Close to 156D. Pistils: To date, pistil development has not been observed on sterile flowers of plants of the new *Hydrangea*.

*Reproductive organs, fertile flowers*.—Stamens: Quantity per flower: About ten. Filament length: About 5 mm. Filament color: Close to NN155C. Anther length: About 0.75 mm. Anther shape: Broadly oblong. Anther color: Close to 158D to lighter than 158D. Pollen amount: Moderate. Pollen color: Close to 156D. Pistils: Pistil quantity per flower: Typically three. Pistil length: About 2 mm. Stigma shape: Club-shaped. Stigma color: Close to 157D. Style length: About 1 mm. Style color: Close to 150D. Ovary color: Close to 157C.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO15' as illustrated and described.

* * * * *